US008642761B2

(12) United States Patent
Ziegler et al.

(10) Patent No.: US 8,642,761 B2
(45) Date of Patent: Feb. 4, 2014

(54) METHOD FOR PRODUCING 3-AMIDINOPHENYLALANINE DERIVATIVES

(75) Inventors: Hugo Ziegler, Witterswil (CH); Peter Wikstroem, Gipf-Oberfrick (CH)

(73) Assignee: Wilex AG, München (DE)

( * ) Notice: Subject to any disclaimer, the term of this patent is extended or adjusted under 35 U.S.C. 154(b) by 63 days.

(21) Appl. No.: 13/300,237

(22) Filed: Nov. 18, 2011

(65) Prior Publication Data

US 2012/0065398 A1  Mar. 15, 2012

Related U.S. Application Data

(62) Division of application No. 12/905,769, filed on Oct. 15, 2010, now Pat. No. 8,088,921, which is a division of application No. 11/699,228, filed on Jan. 29, 2007, now Pat. No. 7,884,206, which is a division of application No. 10/506,256, filed as application No. PCT/CH03/00147 on Feb. 28, 2003, now Pat. No. 7,211,670.

(30) Foreign Application Priority Data

Feb. 28, 2002  (CH) .......................................... 347/02

(51) Int. Cl.
C07D 241/04 (2006.01)
C07D 211/34 (2006.01)
C07C 307/02 (2006.01)

(52) U.S. Cl.
USPC ............... 544/388; 546/227; 564/81; 564/84; 564/251

(58) Field of Classification Search
USPC ................. 544/388; 564/81, 84, 251
See application file for complete search history.

(56) References Cited

U.S. PATENT DOCUMENTS

| 5,852,051 | A | 12/1998 | Bohm et al. |
| 6,342,609 | B2 | 1/2002 | Makino et al. |
| 6,838,460 | B2 | 1/2005 | Himmelsbach et al. |
| 7,211,670 | B2 * | 5/2007 | Ziegler et .................. 544/390 |

FOREIGN PATENT DOCUMENTS

| CH | 689611 A5 | 7/1999 |
| EP | 0739886 A2 | 10/1996 |
| JP | 10-509727 T | 9/1998 |
| WO | 98/54132 A1 | 12/1998 |
| WO | 00/17158 A1 | 3/2000 |
| WO | 01/53280 A1 | 7/2001 |
| WO | 01/55175 A2 | 8/2001 |

OTHER PUBLICATIONS

Stanovnik, B., et al., "AZA-Transfer Reactions The Reaction Between Aroyl and Heteroaroylhydrazines and Aryldiazonium Compounds", Vestn. Slov. Kem. Drus. 27 (3), 251-264 (1980).
Monge. A., et al., "New Quinoxaline and Pyrimido[4,5-b]quinoxaline Derivaties. Potential Anthhypertensive and Blood Platelet Antiaggregating Agents", J. Heterocyclic Chem. 26, 1623-1626 (Nov.-Dec. 1989).
Jendralla, H., et al., "Efficient Kg-Scale Synthesis of Thrombin Inhibitor CRC 220", Tetrahedron, vol. 51, No. 44, 12047-12068 (1995).
Judkins, B.D. et al., "A Versatile Synthesis of Amidines from Nitriles via Amidoximes", Synthetic Communications, 26 (23), 4351-4367 (1996).
Lange, U., et al., "A New Mild Method for the Synthesis of Amidines", Tetrahedron Letters 40, 7067-7070 (1999).
Stürzebecher, J., et al., "3-Amidinophenylalanine-based Inhibitors of Urokinase" Bioorganic & Medicinal Chemistry Letters, 9, 3147-3152 (1999).
Translation of Russian Chemical Bulletin, 51(11), 2100-2105, (2002).
Internationai Search Report for PCT/CH03/00147 mailed on Jun. 20, 2003.
"Protecting Group", on-line publication, Wikipedia, http://en.wikipedia.org/wiki/Protecting_group, (May 2, 2006).
English translation of Japanese Office Action for Patent Application No. 2003-571265 dated Jun. 2, 2005.

* cited by examiner

*Primary Examiner* — Yong Chu
(74) *Attorney, Agent, or Firm* — Hoffmann & Baron, LLP

(57) ABSTRACT

The present invention describes a method for the synthesis of enantiomerically pure 3-amidinophenylalanine derivatives, which are used as pharmaceutically effective urokinase inhibitors, by starting from 3-cyanophenylalanine derivatives. The methods of manufacture comprising only one synthesis step lead to new intermediates, namely 3-hydroxyamidino- and 3-amidrazonophenylalanine derivatives. These intermediates or their acetyl derivatives can be reduced into the desired 3-amidino-phenylalanine derivatives under gentle conditions ($H_2$ or ammonium formiate, Pd/C (approx. 10%), ethanol/water, room temperature, normal pressure or also $H_2$, Pd/C, AcOH or HCl/ethanol, 1-3 bar) in excellent yields and in an enantiomeric excess of up to 99.9%.

4 Claims, 1 Drawing Sheet

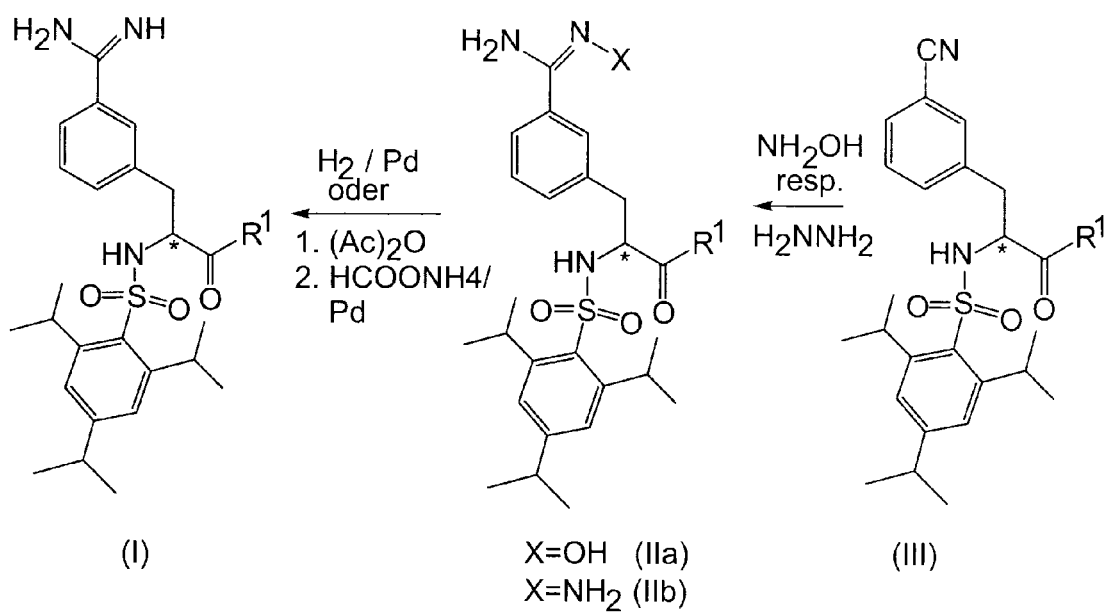

METHOD FOR PRODUCING 3-AMIDINOPHENYLALANINE DERIVATIVES

CROSS-REFERENCE TO RELATED APPLICATIONS

This application is a divisional of U.S. application Ser. No. 12/905,769, filed Oct. 15, 2010, now U.S. Pat. No. 8,088,921, which is a divisional of U.S. application Ser. No. 11/699,228, filed Jan. 29, 2007, now U.S. Pat. No. 7,884,206, which is a divisional of U.S. application Ser. No. 10/506,256, filed Aug. 30, 2004, and afforded a 371(c) date of Mar. 18, 2005, now U.S. Pat. No. 7,211,670, which is the National Stage of International Application No. PCT/CH03/00147, filed Feb. 28, 2003, which claims the benefit of Swiss Application No. 0347/02, filed Feb. 28, 2002, the entire contents of all of which are incorporated by reference herein.

FIELD OF THE INVENTION

The present invention relates to a method for the synthesis of 3-amidinophenyl-alanine derivatives with an improved total chemical yield and an increased enantiomeric excess. These 3-amidinophenylalanine derivatives represent a class of highly efficient urokinase inhibitors (WO 00/17158).

BACKGROUND OF THE INVENTION

The methods of synthesis described in WO 00/17158 for the preparation of urokinase inhibitors comprise a method for converting the cyano function of substituted 3-cyanophenylalanine derivatives into an amidino function. The disadvantages of the method are the insufficient yield produced by the multi-step transformation of the nitrile function into the amidino function, the use of carcinogenic reagents such as hydrogen sulphide and methyl iodide, as well as the release of methyl mercaptan in the form of a highly toxic gas as a by-product. The method requires a considerable quantity of devices and additional separation processes. Moreover, racemization and thus lower enantiomeric excess must be taken into account.

Transformation of a para-positioned nitrile group into an amidino function with hydroxylamine hydrochloride/triethylamine and subsequent Pd-catalytic hydration (10 bar/AcOH/ 50° C.) is described in Tetrahedron 51, 12047-68 (1995) (FIG. 3). However, the reaction conditions are so harsh that the chemical yield and the chemical purity are not satisfying. There is no indication about the enantiomeric excess.

In Tetrahedron Letters 40, 7067-71 (1999), a new gentle method for the preparation of aromatic amidines from nitriles is described which should be more advantageous than all other methods known. The reaction is performed with acetylcysteine and ammonia at temperatures of approximately 60° C. The disadvantage of this method lies in the fact that reasonable yields can only be obtained with π electron-poor (=π electron-attracting) aromates.

Surprisingly, it has been found that transformation of the aromatic 3-cyano function of substituted phenylalanine derivatives of general formula (III) into the 3-amidino function of corresponding compounds of general formula (I) with hydroxylamine and subsequent reduction of the oxyamidine of general formula (IIa) with hydrogen over Pd—C (10%) or reduction of the corresponding acetyloxyamidine manufactured in situ with acetanhydride with ammonium formiate over Pd—C (10%) can be managed under gentle reaction conditions (see following FIG. 1). Here, reaction products with a high chemical yield and purity are obtained using only few devices and without racemization.

Moreover, EP 0 739 886 A2 describes a method for the synthesis of 4-amidrazono-phenylalanine derivatives from corresponding nitriles. Here, the nitrile is first converted into the corresponding thioamide which is activated over a thio-imidoester derivative in such a way that it reacts with hydrazine to form hydrazonoamide (amidrazone).

A direct transformation of the nitrile group into an amidrazone is described in J. Heterocyclic Chem. 26, 1623 (1989). Here, π electron-deficient heteroaromates substituted with cyano (i.e. cyano groups favourable to a nucleophilic attack) have been heated with hydrazine for some hours, whereby amidrazone was obtained in moderate yields.

Moreover, it has been surprisingly found that also a non-activated nitrile that is not bound to an electron-attracting group can be transformed with hydrazine under similar conditions. Thus, compounds of formula (III) can be transformed into amidrazones of formula (IIb) in good yields (see FIG. 1).

Surprisingly, it has also been found that these amidrazones—analogously to the amidoximes of formula (IIa)—can be reduced to the amidines of formula (I) (see FIG. 1). The direct transformation of an unsubstituted amidrazone into an unsubstituted amidine has until now only been described, namely in the case of aza transfer reactions between arylamidrazones and aryldiazonium salts in Vestn. Slov. Kem. Drus. (1980), 27(3), 251-64.

SUMMARY OF THE INVENTION

Thus, the object of the present invention is a method for transforming 3-cyano-phenylalanine derivatives of general formula (III) into 3-amidino derivatives of general formula I, or salts thereof formed with acids, which are present either as L- or D-configurated compounds and wherein $R^1$ represents (a) a group of formula

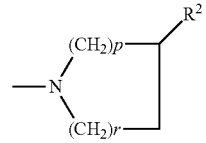

in which either p=1 and r=2 and $R^2$ is benzyloxycarbonyl, benzylaminocarbonyl or 2-thienylhydrazinocarbonyl, or p=2 and r=1 and $R^2$ is ethoxycarbonyl, 2-propyloxycarbonyl, 2-propylaminocarbonyl, methylaminocarbonyl or methyl; or (b) a group of formula

in which $R^3$ is methoxycarbonyl, ethoxycarbonyl, benzyloxycarbonyl, dimethylaminocarbonyl, acetyl or propionyl; using minimal equipment in high chemical yield and purity as well as without racemization.

BRIEF DESCRIPTION OF THE DRAWINGS

FIG. 1 shows how compounds of formula (III) can be transformed into amidoximes of formula (IIa) and into amidrazones of formula (IIb) and how such amidoximes and amidrazones can be reduced to amidines of formula (I).

DETAILED DESCRIPTION OF THE INVENTION

In a first embodiment of the method of the present invention, transformation of the nitrile group into the amidino function occurs over the amidoxime intermediate of general formula (IIa) by means of hydroxylamine hydrochloride in the presence of sodium carbonate in alcoholic-aqueous solution at reflux temperature, advantageously by boiling for 2 to 20 hours, preferably 4 to 10 hours, a compound of formula (III) with a one to 5-fold excess of hydroxylamine hydrochloride/0.5-0.6 equiv. sodium carbonate in an alcoholic-aqueous, preferably ethanolic-aqueous solution. However, the transformation of nitrile (III) with hydroxylamine hydrochloride can also occur at room temperature in the presence of triethylamine in alcoholic solution, with or without addition of a further organic solvent, such as methylene chloride.

Subsequent reduction of the amidoxime function is performed either with hydrogen gas or with ammonium formiate (which is advantageously applied in an at least 4-fold excess) either by directly starting from unsubstituted amidoxime, or over the acetylated amidoxime manufactured in situ with acetanhydride in the presence of hydrochloric acid, advantageously at 20 to 60° C., in an alcoholic-aqueous solution, preferably in an ethanolic-aqueous solution, advantageously in the ratio of 1:1 to 20:1, preferably 3:1 to 10:1, ideally 5:1, in the presence of Pd/C, advantageously 1 to 50%, preferably 5 to 30% Pd/C (approx. 10%), advantageously at normal pressure and a temperature between 10 and 50° C., preferably between 20 and 30° C., ideally at room temperature. However, reduction can also occur by hydrogenation in the presence of Pd/C in an alcoholic, acetic acid-containing solution at a pressure of about 1-3 bar.

In a second embodiment of the method of the present invention, transformation of 3-cyanophenylalanine derivatives of general formula (III) into 3-amidinoderivatives of general formula I occurs over the amidrazone intermediate of general formula (IIb) by boiling, advantageously for 2 to 20 hours, preferably for 4 to 10 hours, a compound of formula (III) with an excess of hydrazine in alcoholic, preferably ethanolic solution. Reduction of the amidrazone intermediate (IIb) into the corresponding amidine (I) occurs under the same conditions as those starting from amidoxime (IIa).

Further objects of the present invention are compounds of general formula (II) as represented in FIG. 1, in particular those of the following formulas (IV) and (V)

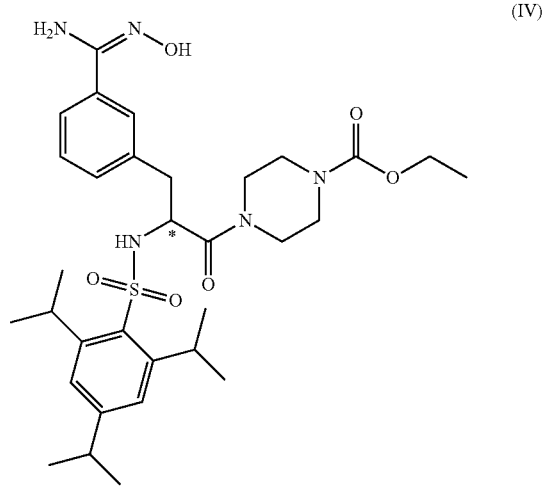

(IV)

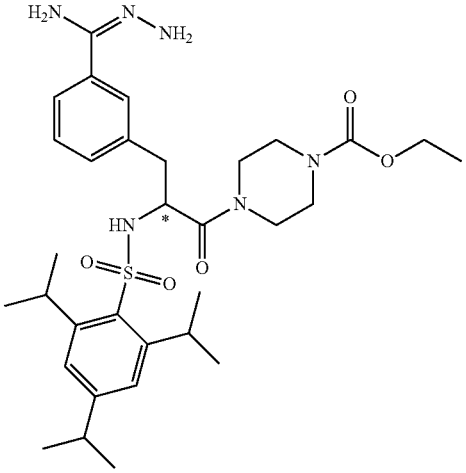

(V)

as (L)- or (D)-enantiomers, and as (E)- or (Z)-isomers or (E/Z)-mixtures, and as free bases or as salts thereof formed with acids.

The following examples further explain the improved methods of synthesis of the present invention and the synthesis of new intermediates, however without restricting the invention.

Analysis of the eluates and products obtained according to the examples was carried out with $^1$H-NMR, HPLC electrospray MS or elementary analysis. The enantiomeric excess was determined according to known methods using HPLC and chiral analytical columns. The starting compounds of general formula (III) and their manufacture are known (e.g. WO 00/17158).

EXAMPLES

Example 1

(A) N-α-2,4,6-Triisopropylphenylsulfonyl-3-oxamidino-(L)-phenylalanine-4-ethoxycarbonyl piperazide 75.4 g (0.126 mol) of N-α-2,4,6-triisopropylphenylsulfonyl-3-cyano-(L)-phenylalanine-4-ethoxycarbonyl piperazide was dissolved in 1.5 l of ethanol, the solution was mixed with 32.5 g (0.47 mol) of hydroxylamine hydrochloride and with a solution of 25.4 g (0.24 mol) of $Na_2CO_3$ in 0.5 l of water and refluxed for 6 hours (80° C.). The crude product obtained after evaporation of the solvent was taken up in 1.5 l of ethyl acetate and extracted with water (3×0.5 l), washed with saturated NaCl, dried over $Na_2SO_4$, filtered and the solvent was evaporated. Yield: 71.3 g (90%).

(B) N-α-2,4,6-Triisopropylphenylsulfonyl-3-amidino-(L)-phenylalanine-4-ethoxycarbonyl piperazide hydrochloride 71.3 g (0.113 mol) of the N-α-2,4,6-triisopropylphenylsulfonyl-3-oxamidino-(L)-phenylalanine-4-ethoxycarbonyl piperazide obtained under (A) was dissolved in 0.71 l of ethanol and the solution was mixed with a suspension of 14.2 g of 10% palladium coal in 140 ml of water. Injection of hydrogen until saturation was followed by hydration until complete transformation at normal pressure (approx. 5 hours). The suspension was filtered over Celite, washed with ethanol/water (9:1) and the solvent was evaporated. The crude product obtained was purified over silica gel 60 (ethyl acetate/2-propanol, 8:2) and finally transformed into the corresponding hydrochloride over Amberlite IRA-400 (Cl⁻ form) in 2-propanol/water (8:2). Yield: 65.4 g (89%), ee-value: 99.9% of the (L) form.

(C) N-α-2,4,6-Triisopropylphenylsulfonyl-3-amidino-(L)-phenylalanine-4-ethoxycarbonyl piperazide hydrochloride 71.3 g (0.113 mol) of the N-α-2,4,6-triisopropylphenylsulfonyl-3-oxamidino-(L)-phenylalanine-4-ethoxycarbonyl piperazide was dissolved in 0.71 l of ethanol, the solution was mixed with 45.6 g (0.46 mol) of acetic anhydride and stirred for 10 min. at room temperature. Afterwards, 0.46 l of 1 N HCl was added and the thereby warm becoming solution was further stirred for 10 min. After cooling to room temperature, 29 g (0.46 mol) of ammonium formiate was added and the mixture was stirred for 5 min. After addition of a suspension of 14.2 g of 10% Pd/C in 140 ml of water, the mixture was stirred for 24 hours at room temperature. After HPLC check of the reaction completion, the suspension was filtered over Celite, washed with a 1:9 mixture of water/ethanol and the solvent was evaporated. The crude product was taken up in 1.5 l of EtOAc, washed with 3 portions of 0.5 l each of 1N HCl, water and saturated NaCl, and dried over $Na_2SO_4$. After chromatographic purification over silica gel 60 with ethylacetate/2-propanol (8:2) and subsequent ion exchange chromatography over Amberlite IRA-400 (Cl⁻ form) in 2-propanol/water (8:2) for the conversion into the corresponding hydrochloride, 62.5 g (85%) of product was obtained. ee value: 99.9% of the (L) form.

Example 2

(A) N-α-2,4,6-Triisopropylphenylsulfonyl-(L)-3-oxamidino-phenylalanyl-nipecotinic acid benzylamide 2.3 g (3.6 mmol) of Nα-2,4,6-triisopropylphenylsulfonyl-(L)-3-cyanophenylalanyl-nipecotinic acid benzylamide was dissolved in 45 ml of ethanol and the solution was mixed with 0.94 g (13.6 mmol) of hydroxylamine hydrochloride followed by a solution of 0.74 g (7 mmol) of $Na_2CO_3$ in 15 ml of water and refluxed for 6 hours (80° C.). The crude product obtained after evaporation of the solvent was taken up in 100 ml of ethylacetate, extracted with water (3×30 ml), washed with saturated NaCl, dried over $Na_2SO_4$ and filtered, and the solvent was evaporated. Yield: 2.1 g (87%).

(B) N-α-2,4,6-Triisopropylphenylsulfonyl-(L)-3-amidino-phenylalanyl-nipecotinic acid benzylamide hydrochloride 2.1 g (3.1 mmol) of the N-α-2,4,6-triisopropylphenylsulfonyl-(L)-3-oxamidino-phenylalanyl-nipecotinic acid benzylamide obtained under (A) was dissolved in 20 ml of ethanol and the solution was mixed with a suspension of 0.4 g of 10% palladium coal in 5 ml of water. Injection of hydrogen until saturation was followed by hydration at normal pressure until complete transformation (approx. 4 hours). The suspension was filtered over Celite, washed with ethanol/water (9:1) and the solvent was evaporated. The crude product obtained was purified over silica gel 60 (ethylacetate/2-propanol, 8:2) and finally converted into the corresponding hydrochloride over Amberlite IRA-400 (Cl⁻ form) in 2-propanol/water (8:2). Yield: 1.74 g (85%), ee value: 99.7% of the (L) form.

Example 3

(A) N-α-2,4,6-Triisopropyl phenylsulfonyl-3-amidrazono-(L)-phenylalanine-4-ethoxycarbonyl piperazide 75.4 g (0.126 mol) of N-α-2,4,6-triisopropylphenylsulfonyl-3-cyano-(L)-phenylalanine-4-ethoxycarbonyl piperazide was dissolved in 1.5 l of ethanol, the solution was mixed with 18.1 g (0.47 mol) of a 100% hydrazine hydrate solution and refluxed for 6 hours (80° C.). The crude product obtained after evaporation of the solvent was taken up in 1.5 l of ethylacetate, extracted with water (3×0.5 l), washed with saturated NaCl, dried over $Na_2SO_4$ and filtered, and the solvent was evaporated. Yield: 65.7 g (83%).

B) N-α-2,4,6-Triisopropylphenylsulfonyl-3-amidino-(L)-phenylalanine-4-ethoxycarbonyl piperazide hydrochloride 65.5 g (0.104 mol) of the N-α-2,4,6-triisopropylphenylsulfonyl-3-amidrazono-(L)-phenylalanine-4-ethoxycarbonyl piperazide obtained under (A) was dissolved in 0.66 l of ethanol and the solution was mixed with a suspension of 13.1 g of 10% palladium coal in 130 ml of water. Injection of hydrogen gas until saturation was followed by hydration at normal pressure until complete transformation (approx. 5 hours). The suspension was filtered over Celite and washed with ethanol/water (9:1), and the solvent was evaporated. The crude product obtained was purified over silica gel 60 (ethylacetate/2-propanol, 8:2) and finally converted into the corresponding hydrochloride over Amberlite IRA-400 (Cl⁻ form) in 2-propanol/water (8:2). Yield: 54.1 g (80%), ee value: 99.8% of the (L) form.

What is claimed is:
1. A method of synthesizing 3-amidrazono-phenylalanine derivatives of general formula (IIb)

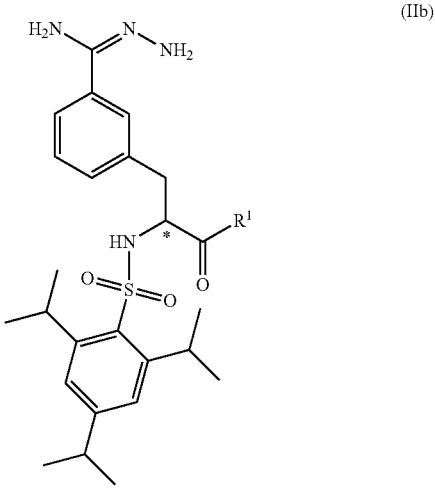

which are present as:
L- or D-enantiomers,
(E)- or (Z)-isomers,
or (E/Z)-mixtures,
and as free bases, or as salts thereof formed with acids wherein R¹ is selected from the group consisting of:
(a) a group of formula

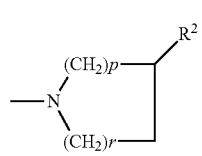

wherein
(i) p=1 and r=2 and R² is benzyloxycarbonyl, benzylaminocarbonyl or 2-thienylhydrazinocarbonyl or
(ii) p=2 and r=1 and R² is ethoxycarbonyl, 2-propyloxycarbonyl, 2-propylcarbonyl, 2-propylaminocarbonyl, methylaminocarbonyl or methyl; and
(b) a group of formula

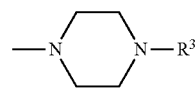

wherein R³ is selected from the group consisting of methoxycarbonyl, ethoxycarbonyl, benzyloxycarbonyl, dimethylaminocarbonyl, acetyl, and propionyl, comprising refluxing a nitrile of the general formula (III)

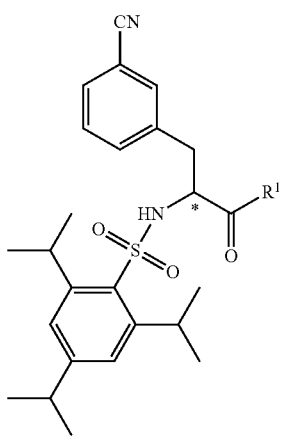

wherein R¹ is selected from the group consisting of:
(a) a group of formula

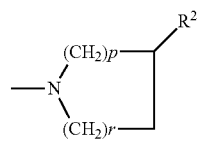

wherein
(i) p=1 and r=2 and R² is benzyloxycarbonyl, benzylaminocarbonyl or 2-thienylhydrazinocarbonyl or
(ii) p=2 and r=1 and R² is ethoxycarbonyl, 2-propyloxycarbonyl, 2-propylcarbonyl, 2-propylaminocarbonyl, methylaminocarbonyl or methyl; and (b) a group of formula

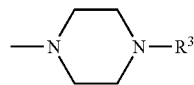

wherein R³ is selected from the group consisting of methoxycarbonyl, ethoxycarbonyl, benzyloxycarbonyl, dimethylaminocarbonyl, acetyl, and propionyl, with an excess of hydrazine in alcoholic solution.

2. The method of claim 1, wherein the refluxing in ethanolic solution lasts for 2 to 20 hours.

3. A compound of the formula (IIb)

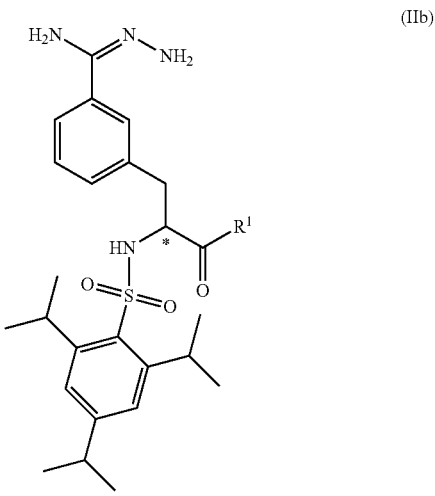

as (L)- or (D)-enantiomers, and as (E)- or (Z)-isomers or (E/Z)-mixtures, and as free bases or as salts thereof formed with acids, wherein R¹ is selected from the group consisting of:
(a) a group of formula

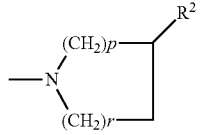

wherein
(i) p=1 and r=2 and R² is benzyloxycarbonyl, benzylaminocarbonyl or 2-thienylhydrazinocarbonyl or
(ii) p=2 and r=1 and R² is ethoxycarbonyl, 2-propyloxycarbonyl, 2-propylcarbonyl, 2-propylaminocarbonyl, methylaminocarbonyl or methyl; and
(b) a group of formula

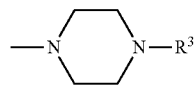

wherein R³ is selected from the group consisting of methoxycarbonyl, ethoxycarbonyl, benzyloxycarbonyl, dimethylaminocarbonyl, acetyl, and propionyl.

4. A compound of formula (V)
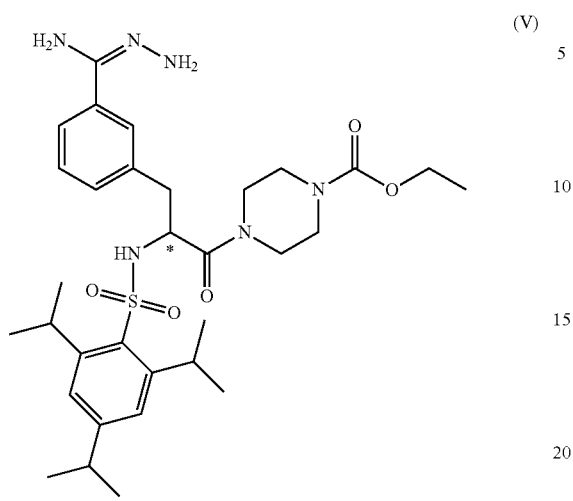
as (L)- or (D)-enantiomers, and as (E)- or (Z)-isomers or (E/Z)-mixtures, and as free bases or as salts thereof formed with acids.
* * * * *